United States Patent [19]

Frey

[11] 4,183,104
[45] Jan. 15, 1980

[54] JOINT IMPLANT

[75] Inventor: Otto Frey, Winterthur, Switzerland

[73] Assignee: Sulzer Brothers Limited, Winterthur, Switzerland

[21] Appl. No.: 908,690

[22] Filed: May 23, 1978

[30] Foreign Application Priority Data

Jun. 22, 1977 [CH] Switzerland .......................... 7648/77

[51] Int. Cl.² ............................................. A61F 1/24
[52] U.S. Cl. ...................................... 3/1.91; 403/121; 403/372
[58] Field of Search ................ 3/1.91, 1.911, 1.9, 3/1.912, 1.913; 403/121, 372, 263; 128/92 C, 92 CA

[56] References Cited

U.S. PATENT DOCUMENTS

| 3,033,624 | 5/1962 | Biesecker | 403/372 X |
| 3,707,006 | 12/1972 | Bokros et al. | 128/92 C X |
| 3,813,700 | 6/1974 | Tavernetti et al. | 3/1 |
| 3,819,288 | 6/1974 | Carmien | 403/263 X |
| 3,837,009 | 9/1974 | Walker | 3/1.911 |
| 3,934,272 | 1/1976 | Wearne et al. | 3/1.911 |
| 4,058,856 | 11/1977 | Doerre et al. | 3/1.91 |
| 4,131,957 | 1/1979 | Bokros | 3/1.911 X |

FOREIGN PATENT DOCUMENTS 541963 11/1973 Switzerland ............................. 3/1.91

Primary Examiner—Clifford D. Crowder
Attorney, Agent, or Firm—Kenyon & Kenyon

[57] ABSTRACT

The joint implant utilizes a pin and socket arrangement wherein the pin and socket are of non-circular cross-sectional shapes. In addition, the socket has a shaped aperture which permits the pin to tilt or rock in the socket without twisting about the longitudinal axis of the pin. The socket has a reduced cross-sectional portion within which the pin is guided as well as widening portions within which the pin may tilt.

14 Claims, 4 Drawing Figures

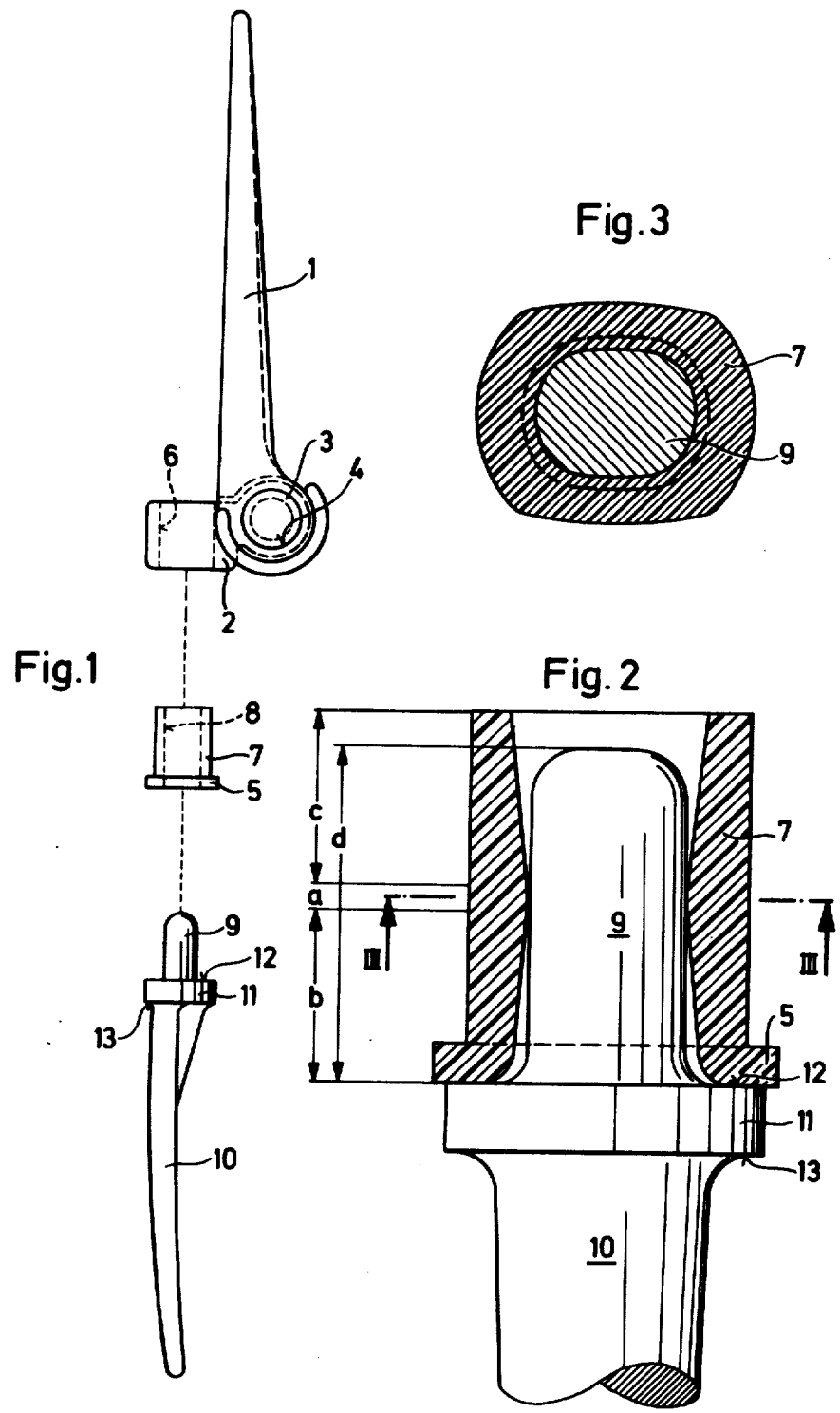

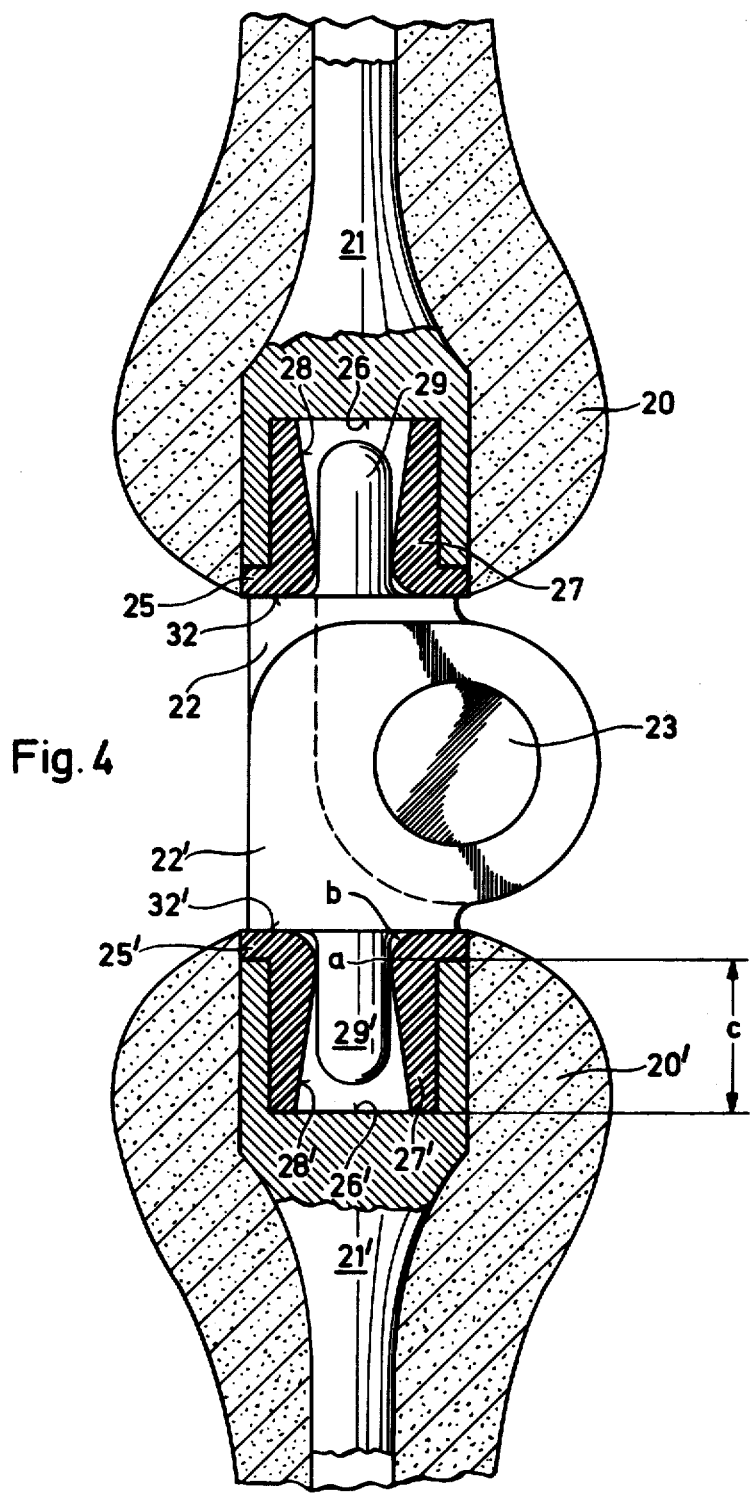

JOINT IMPLANT

This invention relates to a joint implant. More particularly, this invention relates to a joint implant of hinge like construction.

As is known, various types of implants have been used in attempts to replace or duplicate a natural joint. It is also known that different natural joints have different types of motion. For example, some natural joints are of hinge like construction such as elbow joints and finger joints. In such joints, the "instantaneous" physiological axes of rotation, may, however, move to some extent relative to the bones of the joint and position themselves optimally with respect to the forces acting on the associated muscles and ligaments of the joint. However, in known implants for joints of this kind, for example as described in Swiss Pat. No. 541,963, which use anchoring elements to fix the implants in situ, once an anchoring element has been engaged in a bone, the axis of rotation of the element is permanently fixed. Consequently, any variation in the fixation of the anchoring element from the natural axis produces an unnatural loading of the muscles and ligaments. In addition, force directions which are incorrect physiologically, load the anchorages in the bones and cause the anchorages to loosen over a period of time. Still further, prostheses of this type cannot yield to any longitudinal loadings along their lenghts.

In the case of the plug-in type implants, one apparent possibility for increasing the possible "adjustments" for the rotational axis or pivot of the implant would be to provide considerable clearance in each plug-in connection between the anchoring element and the joint part. Unfortunately, a construction of this kind would lead to considerable turning or twisting along the axis of the plug-in connection as well as to possible anti-physiological problems. In addition, such a construction might shift substantially perpendicularly to the longitudinal axis of the connection with a result than an unwanted shear stressing of the ligaments is incurred.

Accordingly, it is an object of the invention to provide a joint implant wherein a part of the implant may have an adjustable axis of rotation.

It is another object of the invention to provide a joint implant of hinge type construction which duplicates the physiological action of a natural joint as closely as possible.

It is another object of the invention to permit relatively large tilting or rocking movements in a plug-in type connection of a joint implant.

It is another object of the invention to eliminate any twisting of an anchoring element of a hinge joint implant about a longitudinal axis extending substantially in the direction of anchorage.

Briefly, the invention provides a joint implant which is comprised of a pair of anchoring elements for anchoring in a respective bone of a joint and a means articulating the elements together in hinged relation. This means includes a socket which is disposed in one of the elements and a pin which is disposed on the other element. In addition, the socket has an elongated aperture with a reduced cross-sectional portion extending along a length of the aperture and widening cross-sectional portions on opposite sides of the reduced cross-sectional portion. The pin is of non-circular cross-section and extends into the aperture in mating engagement with the reduced portion and in spaced relation to the widening portions.

The cross-sectional shape of the pin and the aperture in the socket greatly restricts the possibility that the articulating means can rotate or twist about the longitudinal axis of the joint. The reduced cross-sectional portion of the socket aperture also forms a guide for the pin while the widening portions permit tilting or rocking movements of the pin around the reduced portion. To this end, the reduced cross-sectional portion of the aperture is of generally rectangular shape while the widening portions are of conical shape. The pin is likewise of a generally rectangular shape to mate with the reduced portion of the aperture.

Because of the articulation of the anchoring elements of the implant, the elements can make a large number of adjusting movements relative to one another. However, since the pin is guided in the reduced cross-section of the socket aperture, there is only relatively little clearance for the pin axis and therefore for the relative position of the joint part to an anchoring element or of one anchoring element to another anchoring element which may be rotatably connected to a joint part.

In order to insure guidance of the pin in a reliable manner in a socket aperture, even when the pin has been partly slid out of the aperture as a result of a tensile loading, the axial length of the pin is greater than the axial distance between the reduced cross-sectional portion and the widening cross-sectional portion closest to the anchoring element on which the pin is secured.

The articulating means for the implant may also include an intermediate member in which the socket is formed. In this regard, the intermediate member may be received in a tight fit relation in an anchoring member. Alternatively, the articulating means may include a joint member which is rotatably mounted on an anchoring member with the intermediate member disposed in a tight-fit relation in a bore of the joint member which is of non-circular cross-section, for example of a rounded rectangular shape. Such an intermediate member may also be made of a material which is more resilient than a pin, joint part, and/or the anchoring elements. For example, the intermediate element may be made of a resilient plastic material.

It may also be convenient to limit the depth of penetration of the pin in the socket aperture. In this regard, the pin may be sized to be of less axial length than the overall length of the socket aperture.

These and other objects and advantages of the invention will become more apparent from the following detailed description taken in conjunction with the accompanying drawings in which:

FIG. 1 illustrates an exploded side view of an implant joint for an elbow in accordance with the invention;

FIG. 2 illustrates a part cross-sectional view of a socket and pin arrangement in accordance with the invention;

FIG. 3 illustrates a view taken on line III-III of FIG. 2;

FIG. 4 illustrates a cross-sectional view of an implant joint for a finger in accordance with the invention.

Referring to FIG. 1, the joint implant for an elbow is comprised of a pair of anchoring elements 1, 10. One anchoring element 1 is adapted to be anchored in the humerus (not shown) and has a distal end which is of fork-like hinge construction (not shown in detail). The other anchoring element 10 is adapted to be anchored in the radius bone (not shown).

The joint implant includes a means for articulating the anchoring elements 1, 10 together in hinged relation. This means includes a joint member 2 which is rotatably mounted in the fork-like hinge construction of the anchoring element 1 via a pivot 3. This joint member 2 is formed of two hollow parts having longitudinal axes which are perpendicular to one another and which are physically offset from one another. The two hollow parts are integrally formed to provide a single unit. One hollow part receives the pivot 3 and is accordingly formed with an appropriate circular bore 4 while the other hollow part is formed with a hollow bore or cavity 6 which is of a non-circular cross-sectional shape, such as a rounded rectangular cross-sectional shape, i.e., a rectangle rounded on the small sides. In addition, the articulating means includes an intermediate member 7 having an outer boundary which matches the shape of the bore 6 (see FIG. 3). The intermediate member 7 is disposed in tight-fit relation in the bore 6 so as to be held against rotation about its longitudinal axis.

The intermediate member 7 includes a flange 5 at one end which prevents the member 7 from penetrating too deeply into the bore 6 as well as with a socket 8. The socket 8 is sized and shaped so as to receive a pin 9 disposed at the proximal end of the distal anchoring element 10. As shown in FIG. 3, the pin 9 has a cross-sectional shape which also resembles a rounded rectangular shape so as to be held against rotation within the intermediate element 7. In this way, once positioned in the socket 8, the pin 9 cannot be turned or twisted accidentally around its longitudinal axis.

As shown in FIG. 1, the pin 9 is separated from a stem of the anchoring element 10 by a flange 11 which serves to limit the depth of penetration of the pin 9 into the socket 8 via an abutment surface 12. The flange 11 also limits the depth of penetration of the anchoring element 10 into the radius bone (not shown) via an abutment surface 13 opposite the abutment surface 12.

The anchoring elements 1, 10 and the joint member 2 may be prepared from any material normally used in the implant art, for example, a metal. The intermediate element 7 which is used in association with such metal parts may be made of a plastic, such as a high molecular weight polyethylene which is also normally used in the implant art. Of course, any other suitable plastic may be used or, alternatively, the entire implant can be made wholly or partly of bio-ceramics. If the complete implant is made of a single material, the socket 8 can be formed directly in the joint member 2 without the need of the intermediate member 7.

Referring to FIG. 2, the socket 8 formed in the intermediate member 7 has an elongated aperture which has a reduced cross-sectional portion in a central region a. This region a is of a longitudinal extent of at most one quarter the length of the pin 9. In addition, while the reduced portion of the aperture is narrowed relative to the pin 9, the aperture has widening cross-sectional portions on opposite sides of the reduced portion in the regions b, c. In this way, clearances are provided between the pin 9 and the socket in these regions b, c. For example, the aperture may widen conically in the regions b, c, so that the pin 9 which is guided in the region a can make a tilting or rocking movement using the region a as a "pivot point". In this case, it may sometimes be convenient for the "pivot point" to have a different relative position to the rotational axis or pivot of the joint in different joints. This can be accomplished to some extent by having the region a at different distances from the plug-in end of the socket aperture.

The distance b between the region a and a plug-in end of the socket 8, that is the end closest to the anchoring element 10, is adapted to the axial length of the pin 9 such that when the pin 9 is fully engaged in the socket 8, the region a is disposed, at most, approximately in the central region of the pin length. This insures that an adequate guidance for the pin 9 is still provided by the region a even though the pin 9 should slide out of the socket 8 to any extent as a result of being pulled.

Referring to FIG. 4, the implant for a finger joint may utilize anchoring elements 21, 21' of identical construction which are disposed in respective finger bones 20, 20'. In this case, each anchoring element, 21, 21' is provided with a bore 26, 26' at the end and the means for articulating the elements 21, 21' together in hinged relation is constructed to fit within these bores in a releasable manner. As shown, the articulating means includes a pair of intermediate members 27, 27' and a joint member composed of a pair of hingedly connected components 22, 22'. As indicated, the two components 22, 22' are hinged together via a pivot 23.

Each intermediate member 27, 27' is disposed in a respective bore 26, 26' of an anchoring element in tight fit relation. Also, each intermediate member, 27, 27' has a socket 28, 28' which defines an elongated aperture with a reduced cross sectional portion a and widening cross sectional portions on opposite sides of the reduced cross sectional portion.

In addition, the bores 26, 26' and the outer contour of the members 27, 27' are of non-circular shape so as to prevent rotation of the members within the bores.

Each component 22, 22' has a pin 29, 29' of non-circular cross section which is disposed in a respective socket 28, 28' in mating engagement with the reduced cross sectional portions a. In addition, these pins 29, 29' are in spaced relation to the widening cross sectional portions of each socket 28, 28'.

As shown, each intermediate element 27, 27' has a flange 25, 25' at one end which abuts against a surface 32, 32' of a component 22, 22' to prevent the intermediate elements 27, 27' from engaging too deeply in the bores 26, 26' and to prevent the pins 29, 29' from penetrating too deeply into the socket apertures 28, 28'.

As is also shown, the reduced cross sectional regions a of the socket apertures are disposed near the plug-in ends of the aperture. Consequently, the widening region b at these ends may be of a relatively sharply curved trumpet shape whereas the other region c retains approximately the shape as shown in FIG. 2. This change in the region b considerably reduces the overall length of the socket but is more expensive to produce than the socket described in FIG. 2. The socket apertures 8, 28, 28' of the various described embodiments, can be shaped, for example by a chip-removing treatment with a cutter from a solid shape.

The invention thus provides a joint implant of hinged construction which permits relatively large tilting or rocking movements to occur despite there being relatively little chance of twisting about a longitudinal axis extending in the direction of anchorage and despite a relatively small clearance between the pin and socket arrangement of the joint.

It is to be noted that the pin is resiliently mounted in a longitudinal direction within a socket. Thus, axial forces imposed upon the implant may be more readily absorped.

What is claimed is:

1. A joint implant comprising
a pair of anchoring elements for anchoring in respective bones of a joint; and
means articulating said elements together in hinged relation, said means including a socket disposed in one of said elements and a pin disposed in the other of said elements, said socket having an elongated aperture therein with a reduced cross-sectional portion extending along a length of said aperture and widening cross-sectional portions on opposite sides of said reduced cross-sectional portion, said pin being of non-circular cross-section and extending into said aperture in mating engagement with said reduced cross-sectional portion and in spaced relation to said widening cross-sectional portions.

2. A joint implant as set forth in claim 1 wherein said reduced cross-sectional portion of said aperture is of generally rectangular shape and said widening portions are of conical shape.

3. A joint implant as set forth in claim 1 wherein said pin has an axial length greater than the axial distance between said reduced cross-sectional portion and said widening cross-section portion closest to said other element.

4. A joint implant as set forth in claim 1 wherein said means includes an intermediate member having said socket formed therein.

5. A joint implant as set forth in claim 4 wherein said intermediate member is made of a material more resilient than said pin.

6. A joint implant as set forth in claim 4 wherein said intermediate member is received in tight-fit relation in said one anchoring element.

7. A joint implant as set forth in claim 4 wherein said means includes a joint member rotatably mounted on said one anchoring element, said joint member having a bore of rounded rectangular cross-section receiving said intermediate member therein a tight-fit relation.

8. A joint implant as set forth in claim 4 wherein said intermediate member has an outwardly extending flange at an end facing said pin.

9. A joint implant as set forth in claim 4 wherein said intermediate member is made of plastic.

10. A joint implant as set forth in claim 1 wherein said reduced cross-sectional portion is disposed at the center of said socket and said widening portions are disposed in symmetric relation on opposite sides of said reduced portion.

11. A joint implant as set forth in claim 1 wherein said reduced cross-sectional portion is disposed near said other element and said widening portions widen to different extents on opposite sides of said reduced portion.

12. A joint implant as set forth in claim 1 wherein said reduced cross-sectional portion has an axial length equal to or less than one-quarter the length of said pin.

13. A joint implant comprising
a pair of anchoring elements,
a joint member rotatably mounted on one of said anchoring elements about a pivot axis, said joint member having a bore of non-circular cross-section offset from and disposed on an axis perpendicular to said pivot axis;
an intermediate member disposed in said bore in tight-fit relation, said member having a socket defining an elongated aperture with a reduced cross-sectional portion extending along a length of said aperture and widening cross-sectional portions on opposite sides of said reduced cross-sectional portion; and
a pin of non-circular cross-section on the other of said anchoring elements, said pin being disposed in said socket in mating engagement with said reduced cross-sectional portion and in spaced relation to said widening cross-sectional portions.

14. A joint implant comprising
a pair of anchoring elements, each element having a bore therein;
a pair of intermediate members, each said member being disposed in a respective bore in tight-fit relation, each said member having a socket defining an elongated aperture with a reduced cross-sectional portion extending along a length of said aperture and widening cross-sectional portions on opposite sides of said reduced cross-sectional portion; and
a joint member having a pair of hingedly connected components, each of said components having a pin of non-circular cross-section disposed in a respective socket in mating engagement with said reduced cross-sectional portion and in spaced relation to said widening cross-sectional portions thereof.

* * * * *